United States Patent [19]

Breddam et al.

[11] Patent Number: 4,645,740
[45] Date of Patent: Feb. 24, 1987

[54] PROCESS FOR ENZYMATIC REPLACEMENT OF THE B-30 AMINO ACID IN INSULINS

[75] Inventors: Klaus Breddam, Glostrup; Jack T. Johansen, Rungsted Kyst, both of Denmark; Fred Widmer, Bethesda, Md.

[73] Assignee: Carlsberg Biotechnology Ltd. A/S, Copenhagen, Denmark

[21] Appl. No.: 364,856

[22] PCT Filed: Jul. 23, 1981

[86] PCT No.: PCT/DK81/00074
§371 Date: Mar. 23, 1982
§102(e) Date: Mar. 23, 1982

[87] PCT Pub No.: WO82/00301
PCT Pub. Date: Feb. 4, 1982

Related U.S. Application Data

[63] Continuation-in-part of Ser. No. 136,661, Apr. 2, 1980, Pat. No. 4,339,534.

[30] Foreign Application Priority Data

Jul. 24, 1980 [DK] Denmark .............................. 3197/80

[51] Int. Cl.$^4$ ..................... C12P 21/04; C12P 21/06
[52] U.S. Cl. ........................................ 435/71; 435/69
[58] Field of Search ................. 435/68, 69, 70, 174, 435/212, 219, 224, 71

[56] References Cited

U.S. PATENT DOCUMENTS

| | | |
|---|---|---|
| 3,276,961 | 10/1966 | Bodanszky et al. . |
| 4,182,654 | 1/1980 | Royer ..................... 435/70 |
| 4,320,197 | 3/1982 | Morihara et al. ............ 435/70 |
| 4,339,534 | 7/1982 | Johansen et al. ............ 435/68 |
| 4,343,898 | 8/1982 | Markussen ................ 435/70 |

FOREIGN PATENT DOCUMENTS 0017485 10/1980 European Pat. Off. .
0017938 10/1980 European Pat. Off. .

OTHER PUBLICATIONS

Kozarich, Microbiology, 203–208 (1977).
Hayashi et al, J. Biochem., 77:69–79 (1975).
Johansen et al, Carls. Res. Commun., 41(1): 1–14 (1976).
Chem. Abstracts 94:103810 j Gattner et al. Insulin: Chem. Struct. Funct. Insulin Relat. Horm., Proc. Int. Insulin Symp., 2nd 1979 (Pub. 1980).
Widmer et al., Carlsberg Res. Commun., vol. 44, 37–46 (1979).
Breddam et al., Carlsberg Res. Commun., vol. 45, 237–247 (1980).
Chem. Abstracts, vol. 87, 113665K Microbiology, 1977, 203–208.
Kubota et al., J. Biochem., vol. 74, 757–770 (1973).
Morihara et al., Nature, vol. 280, 412–413 (1979).

*Primary Examiner*—Esther M. Kepplinger

[57] ABSTRACT

The B-30 amino acid in insulins is replaced enzymatically by
reacting as substrate component the selected insulin Ins-X, wherein X represents the B-30 amino acid
with an amine component selected from the group consisting of
(a) amino acids of the formula

H—B—OH wherein B is an amino acid residue,
(b) optionally N-substituted amino acid amides of the formula

H—B—NR$^1$R$^2$ wherein B is an amino acid residue and R$^1$ and R$^2$ are independently selected from the group consisting of hydrogen, amino, hydroxy, alkyl, cycloalkyl, aryl, heteroaryl and aralkyl or R$^1$ and R$^2$ together with the nitrogen atom form a heterocyclic group which may contain a further hetero atom, and
(c) amino acid esters of the formula H—B—OR$^3$, H—B—SR$^3$ or H—B—SeR$^3$ wherein B is am amino acid residue and R$^3$ represents alkyl, cycloalkyl, aryl, heteroaryl or aralkyl
in the presence of an L-specific serine or thiol carboxypeptidase enzyme, preferably carboxypeptidase-Y, in an aqueous solution or dispersion having a pH from about 7 to 10.5, thereby to form an insulin derivative
Ins—B—OH, Ins—B—NR$^1$R$^2$, Ins—B—B—NR$^1$R$^2$, Ins—B—OR$^3$, Ins—B—SR$^3$ or Ins—B—SeR$^3$ (Abstract continued on next page.)

and subsequently cleaving a group —NR$^1$R$^2$, —B—NR$^1$R$^2$, —OR$^3$, —SR$^3$ or SeR$^3$, if desired, preferably by using a carboxypeptidase enzyme. The cleaving may also be performed on derivatives obtained by other methods.

By using porcine insulin as substrate component and threonine as the amino acid forming part of the amine component human insulin is obtained.

12 Claims, 3 Drawing Figures

PROCESS FOR ENZYMATIC REPLACEMENT OF THE B-30 AMINO ACID IN INSULINS

This application is a continuation-in-part of U.S. Ser. No. 136,661, filed Apr. 2, 1980 by Jack T. Johansen and Fred Widmer; U.S. Ser. No. 136,661 issued as U.S. Pat. No. 4,339,534 on July 13, 1982, and was co-pending with this application.

BACKGROUND OF THE INVENTION

1. Field of the invention

The present invention generally relates to a process for enzymatic replacement of the C-terminal amino acid in the B-chain (B-30) of insulins from various species.

It is well known that insulins from different vertebrate species including mammals and humans differ in their primary structure. Since Sanger in 1958 determined the primary structure of bovine insulin the primary structure of insulins from other vertebrate species has been determined.

These results as summarized in the below figure using the porcine insulin as model indicate that amino acid substitutions can occur at many positions within either chain. However, certain structural features are common to all the insulins, e.g. the position of the 3 disulfide bonds, the N-terminal region of the A-chain, the B23–26 sequence in the C-terminal region of the B-chain, etc.

The differences in the primary structure of some common insulins are seen from the below table:

|              | A-chain |     |     |      | B-chain |     |     |
| ------------ | ------- | --- | --- | ---- | ------- | --- | --- |
|              | 4       | 8   | 9   | 10   | 3       | 29  | 30  |
| Bovine       | Glu     | Ala | Ser | Val  | Asn     | Lys | Ala |
| Sheep        | Glu     | Ala | Gly | Val  | Asn     | Lys | Ala |
| Horse        | Glu     | Thr | Gly | Ileu | Asn     | Lys | Ala |
| Sei whale    | Glu     | Ala | Ser | Thr  | Asn     | Lys | Ala |
| Porcine      | Glu     | Thr | Ser | Ileu | Asn     | Lys | Ala |
| Sperm whale  | Glu     | Thr | Ser | Ileu | Asn     | Lys | Ala |
| Dog          | Glu     | Thr | Ser | Ileu | Asn     | Lys | Ala |
| Human        | Glu     | Thr | Ser | Ileu | Asn     | Lys | Thr |
| Rabbit       | Glu     | Thr | Ser | Ileu | Asn     | Lys | Ser |
| Rat 1        | Asp     | Thr | Ser | Ileu | Lys     | Lys | Ser |
| Rat 2        | Asp     | Thr | Ser | Ileu | Lys     | Met | Ser |

While the invention is described more fully below with relation to the specific conversion of porcine insulin into human insulin, viz. replacement of B-30 alanine by threonine, it will easily be understood that the described method applies equally well to other types of insulin in that e.g. rabbit insulin may also be converted into human insulin, bovine insulin may be converted into B-30 (Thr) bovine insulin, etc.

2. Background of invention, especially with relation to conversion of porcine insulin into human insulin The idea of converting porcine insulin into human insulin by semi-synthetic procedure has been an attractive problem in the field of insulin chemistry.

As stated above, human insulin differs from porcine insulin by only one amino acid, the C-terminal residue of the B-chain (B-30) being threonine in human and alanine in porcine insulin, respectively. The exchange of alanine to threonine was initially performed chemically and recently enzymatic procedures have been used. Ruttenberg (1972) (Ref. 1) has described the chemical conversion of porcine insulin into human insulin: esterification to insulin-hexamethylester, hydrolysis with trypsin to desoctapeptide insulin (DOI)-pentamethylester, blocking of the amino terminal residues, chemical coupling with a synthetic octapeptide of the corresponding human insulin sequence, acidic deprotection of the amino-groups, and finally alkaline saponifcation of the methyl ester groups. However, nobody has ever been able to produce pure human insulin by this method, since the chemical procedures, and in particular the final alkaline saponification steps seriously damage the insulin molecule and also isoasparagine at the C-terminal residue of the A-chain is formed (Gattner et al. (Ref. 2)). To prevent this effect Obermeier and Geiger (1976) (Ref. 3) have carried out the fragment condensation without protection of the side chain carboxyl groups of DOI. They could isolate human insulin after extensive purification, but only in very low yields. Similar approaches have been taken by Gattner et al. (Ref. 2), using various insulin fragments. However, using the chemical methods nobody has so far prepared pure human insulin in more than trace amounts.

M. Bodanszky et al. provides a process for preparing human insulin in U.S. Pat. No. 3,276,961 wherein human insulin was ostensibly prepared from other animal insulins by an action of an enzyme such as carboxypeptidase A and trypsin in the presence of threonine. This process is not likely to produce human insulin because trypsin and carboxypeptidase A hydrolyze not only the peptide bond of lysyl-alanine (B29–B30) but also the other positions in insulin under the condition described there. Trypsin preferentially hydrolyzes the peptide bond of arginyl-glycine (B22–B23) than that of lysyl-alanine (B29–B30). Meanwhile, carboxypeptidase A cannot release solely the alanine at C-terminal of the B chain without liberating asparagine at C-terminal of the A chain. A special condition, i.e. reacting in an ammonium hydrogencarbonate buffer solution, is necessary to prevent the release of the asparagine. The condition was discovered in 1978 (Schmitt, Hoppe-Seyler's Z. Physiol. Chem., 359, 799–802 (1978)). Furthermore, peptide synthesis may hardly occur because hydrolysis ratio is faster than synthesis ratio in the condition. Inouye et al. (Ref. 4) have shown that human insulin can be obtained by coupling N-terminal protected DOI from porcine insulin with a synthetic octapeptide corresponding to residues B-23–B30 of human insulin using trypsin as a catalyst.

However, this method is cumbersome in that it requires firstly a trypsin-catalyzed digestion of porcine insulin to form DOI, which is N-terminal protected by acylation with BOC-N$_3$ and then incubated for 20 h with a separately synthesized human B23–B30 octapeptide, wherein B29 lysine is BOC-protected. The obtained (BOC)$_3$-human insulin is subsequently deprotected with trifluoroacetic acid/anisole at 0° C. for 60 min. The yield was 49% based on the (BOC)$_2$—DOI used.

Similarly, Morihara et al. (Ref. 5) have synthesized human insulin from des-alanine (B-30)-insulin (DAI) obtained by digestion of porcine insulin with carboxypeptidase A for 8 h. The DAI (10 mM) was incubated with a large excess (0,5M) of threonine—OBu$^t$ ester at 37° C. for 20 h in the presence of high concentrations of organic co-solvents. The formed [Thr—OBu$^t$—B—30] insulin was then deprotected with trifluoroacetic acid in the presence of anisole. The yield was 41%. In a similar experiment [Thr—B—30] bovine insulin was obtained in 60% yield.

Also this method is cumbersome in that it requires a pretreatment of the initial insulin, long coupling times and a separate deprotection step. Also high amounts of organic co-solvents are necessary to minimize the hydrolytic activity of the enzyme.

In a similar experiment Morihara et al. (Ref. 6) used Achromobacter Protease I as enzymatic catalyst for the coupling of DAI with a large excess of Thr—OBu$^t$ under formation of [Thr—OBu$^t$—B—30] insulin, which was isolated and deprotected as above. Although high yields (52%) may be obtained the reaction time was 20 h.

A similar experiment with bovine insulin leads to [Thr—OBu$^t$—B—30] bovine insulin in 58% yield.

The processes disclosed in Ref. 5 and 6 are also described in European Patent Application No. EP 17938 published on Oct. 29, 1980 and Danish Application No. 1556/80.

Recently, it has been demonstrated that the enzyme carboxypeptidase-Y is an effective catalyst in peptide synthesis (Widmer and Johansen (Ref. 7) and Danish Patent Application No. 1443/79, filed Apr. 6, 1979). Furthermore, it has been shown that the enzyme under certain conditions catalyzes the exchange of the C-terminal amino acid in a peptide with another amino acid or amino acid derivative in a transpeptidation reaction (cf. International Appln. No. PCT/DK80/00020, filed Apr. 1, 1980 and published on Oct. 16, 1980 as WO 80/02151, and European Application No. EP 17485, published on Oct. 15, 1980, U.S. application Ser. No. 136,611 filed Apr. 2, 1980 and Ser. No. 220,022 filed Dec. 2, 1980 and based on the above PCT/DK80/0020. The underlying reaction principles are more fully explained by the inventors Breddam et al. (Ref. 11) who also discovered the so far unrecognized peptidyl-aminoacid-amide hydrolase activity of CPD-Y. The above-mentioned applications and the inventor's articles are incorporated herein by reference.

Although the general principle of an enzyme catalyzed transpeptidation reaction is thus described and exemplified in the above PCT and U.S. applications, the applicability thereof in connection with insulins has not been mentioned or shown.

SUMMARY OF THE INVENTION

The object of the present invention is to provide a process for enzymatic replacement of the B-30 amino acid in insulins, which is not entailed with the drawbacks mentioned in the foregoing, and more particularly a process that does not require pretreatment of the insulin starting material, long reaction times and chemical deprotection steps.

More specifically it is an object of the invention to provide a unique and simple process for conversion of porcine insulin to human insulin in high purity and good yields.

Another object of the invention is to provide an improved process for cleaving B-30 carboxyl group protected insulin derivatives, particularly deamidating amide derivatives of various insulins without regard to their source.

Briefly this and other objects of the invention can be attained in a process for enzymatic replacement of the B-30 amino acid in insulins which comprises reacting as substrate component the selected insulin
Ins-X, wherein X represents the B-30 amino acid with an amine component selected from the group consisting of
(a) amino acids of the formula

H—B—OH wherein B is an amino acid residue,
(b) optionally N-substituted amino acid amides of the formula

H—B—NR$^1$R$^2$ wherein B is an amino acid residue and R$^1$ and R$^2$ are independently selected from the group consisting of hydrogen, amino, hydroxy, alkyl, cycloalkyl, aryl, heteroaryl and aralkyl or R$^1$ and R$^2$ together with the nitrogen atom form a heterocyclic group which may contain a further hetero atom, and
(c) amino acid esters of the formula H—B—OR$^3$, H—B—SR$^3$ or H—B—SeR$^3$ wherein B is an amino acid residue and R$^3$ represents alkyl, cycloalkyl, aryl, heteroaryl or aralkyl in the presence of an L-specific serine or thiol carboxypeptidase enzyme from yeast or of animal, vegetable or microbial origin in an aqueous solution or dispersion having a pH from about 7 to 10.5, thereby to form an insulin derivative
Ins—B—OH, Ins—B—NR$^1$R$^2$, Ins—B—B—NR$^1$R$^2$, Ins—B—OR$^3$, Ins—B—SR$^3$ or Ins—B—Ser$^3$
and subsequently cleaving a group —NR$^1$R$^2$, B—NR$^1$R$^2$, —OR$^3$, —SR$^3$ or SeR$^3$, if desired.

The above-mentioned cleaving step is of course not limited to insulin derivatives prepared according to the first transpeptidation step, but may be applied on any such derivative without regard to its source, in particular derivatives prepared according to EP 17938 as shown below in example 5.

DETAILED DESCRIPTION OF THE PREFERRED EMBODIMENTS

The present invention is based on the surprising recognition that the above-mentioned enzyme carboxypeptidase Y can convert porcine insulin into human insulin by exchanging B-30 alanine with threonine in a single step without isolation of an intermediate product and subsequent deprotection treatment. Optionally an insulin amide intermediate may be isolated, and, if desired, subsequently deamidated, using the same enzyme carboxypeptidase Y.

As further elucidated below, the most suitable threonine derivative for this conversion is threonine amide. However, the conversion will often result in a mixture of human insulin and a certain amount of unreacted porcine insulin which are difficult to separate, why the insulin amide intermediates formed are preferably separated from the reaction mixture i.a. containing unreacted porcine insulin, and subsequently deamidated, advantageously using the same enzyme carboxypeptidase Y, as also further expounded below.

Due to the broad peptidase specificity of CPD-Y as thoroughly described and shown in the patent applications and articles referred to above the invention is not limited to porcine insulin as starting material, but any other insulin, e.g. from the species described earlier, and any other amino acid may be used for the replacement reaction.

Also other enzymes are applicable as described below.

The simplicity of the process according to the invention is indeed surprising, even on the background of the application PCT/DK80/00020, and U.S. Pat. No.

pH-value should be selected so that the activities are counterbalanced as explained in the foregoing.

If CPD-Y is used as enzyme, the pH-value is preferably 7.5 to 10.5, particularly 9.0 to 10.5, as explained below. However, a low pH within the preferred range such as about 7.5 is particularly expedient, if an isolation of insulin amide intermediates is desired.

The selected pH-value should preferably be maintained throughout the coupling reaction, and may then be changed for precipitation of the reaction product, cleavage of protective groups, etc. A pH might be selected at which the enzyme displays amidase activity thereby preventing precipitation of the formed insulin amide and thus contributes advantageously to the formation of the desired insulin in one step. Also a pH might be selected where the enzyme displays predominantly peptidase activity thereby favouring the formation of stable insulin amide intermediates.

The pH-control may be provided for by incorporating a suitable buffer for the selected pH-range in the reaction medium, such as a bicarbonate buffer.

The pH-value may also be maintained by adding an acid, such as HCl, or a base, such as NaOH, during the reaction. This may conveniently be done by using a pH-stat.

Based on the information given above and in Ref. 7 and 11, the skilled person will be able to select the most suitable reaction conditions, especially with regard to the pH, by which the various enzymatic activities (amidase, peptidase, esterase, carboxypeptidase and peptidyl-amino-acid-amide hydrolase) might best be utilized depending upon the insulin substrate component, the amine component and the intention to suppress or favour the formation of intermediates.

Generally speaking low pH-values within the above range favour the formation and precipitation of an insulin amide intermediate, while higher values lead to a cleaving of the amide group due to the more pronounced amidase activity of the carboxypeptidase enzyme.

However, these conditions may also be influenced upon by varying the enzyme concentration, reaction time, etc.

The reaction is, as mentioned, carried out in an aqueous reaction medium which, if desired, may contain up to 50% by volume of an organic solvent. Preferred organic solvents are alkanols, e.g. methanol and ethanol, glycols, e.g. ethylene glycol or polyethylene glycols, dimethyl formamide, dimethyl sulfoxide, tetrahydrofurane, dioxane and dimethoxyethane.

The selection of the composition of the reaction medium depends particularly upon the solubility, temperature and pH of the reaction components and the insulin products involved and upon the stability of the enzyme.

The reaction medium may also comprise a component that renders the enzyme insoluble, but retains a considerable part of the enzyme activity, such as an ion exchanger resin. Alternatively, the enzyme may be immobilized in known manner, cf. Methods of Enzymology, Vol. 44, 1976, e.g. by bonding to a matrix, such as a cross-linked dextran or agarose, or to a silica, polyamide or cellulose, or by encapsulating in polyacrylamide, alginates or fibres. Besides, the enzyme may be modified by chemical means to improve its stability or enzymatic properties.

In case it is desired to suppress any precipitation of insulin amide intermediates, the reaction medium may also contain urea or guanidine hydrochloride in concentrations up to 3 molar. This may also be advantageous at pH-values and in media where the insulin substrate component has a limited solubility.

The concentration of the two participants in the reaction may vary within wide limits, as explained below. A preferred starting concentration for the insulin substrate component is 0.002 to 0.05 molar and for the amine component 0.05 to 3 molar.

The enzyme activity may vary as well, but the concentration is preferably $10^{-6}$ to $10^{-4}$ molar, in particular $10^{-5}$ molar. The most advantageous activity depends i.a. on the substrate concentration, the amine concentration and the reaction time.

According to the invention the reaction temperature is preferably 20° to 40° C. The most appropriate reaction temperature for a given synthesis can be determined by experiments, but depends particularly upon the used amine component and enzyme concentration. An appropriate temperature will usually be about 20° to 30° C., preferably about 25° C. At temperatures lower than 20° C. the reaction time will usually be inappropriately long, while temperatures above 40° C. often cause problems with the stability of the enzyme and/or reactants or of the reaction products.

Similar variations occur for the reaction time which depends very much upon the other reaction parameters, especially the enzyme concentration. The standard reaction time in the process of the invention is about 2–6 hours.

It should be added that when using an amide or substituted amide as the amine component, it is normally desired to cleave the amide group specifically from the formed insulin amide. Also in this respect the carboxypeptidase, especially CPD-Y is very suitable since as described above CPD-Y exhibits amidase activity at pH > 9 while the carboxypeptidase activity is negligible.

By the same token the carboxypeptidase might generally be used to cleave the ester groups $OR^3$, $SR^3$ or $SeR^3$ as defined from the formed insulin ester intermediate to obtain a final insulin which is not C-terminal protected.

Before the process of the invention will be illustrated by examples, starting materials, methods of measurement, etc. will be explained in general terms.

Starting Materials

Porcine insulin was kindly supplied by Nordisk Insulinlaboratorium, Cophenhagen. Carboxypeptidase Y from baker's yeast, a commercial preparation of the Carlsberg Breweries, was isolated by a modification of the affinity chromatographic procedure of Johansen et al. (Ref. 8) and obtained as a lyophilized powder (10% enzyme in sodium citrate). Before use the enzyme was desalted on a "Sephadex G-25" column (1.5×25 cm) equilibrated and eluted with water. The concentration of the enzyme was determined spectrophotometrically using $E_{280\ nm}^{1\%} = 14.8$. The enzyme preparation used was free of Protease A as checked by the assay of Lee and Riordan (Ref. 9). L-threonine amide was purchased from Vega-Fox, Ariz., USA. L-threonine methyl ester from Fluka, Switzerland, and L-threonine, Dansyl chloride, carboxypeptidase A and trypsin were obtained from Sigma, USA. Chromatographic materials were products of Pharmacia, Sweden. All other reagents and solvents were analytical grade from Merck, W. Germany.

3,276,961 (Bodanszky), since it might well be expected that not only the B-30 amino acid, but also the A-21 Asparagine common to all the above-mentioned known insulins would be attacked by the enzyme.

In the above-mentioned earlier application the desired enzymatic characteristics with regard to a general peptide synthesis are explained in detail, and it is stated that a plurality of carboxypeptidases exhibit different enzymatic activities which are very dependent on pH so that e.g. in a basic environment at a pH from 8 to 10.5 they display predominantly esterase or amidase activity and at a pH from 9 to 10.5 no or only insignificant carboxypeptidase activity, which, however, becomes more and more pronounced with pH-values decreasing below 9. The esterase activity is less important in the present context but otherwise these properties can be advantageously used in the process of the invention, because they contribute to the achievement of a one step process with good yields.

The applicable carboxypeptidases in the process of the invention are L-specific serine or thiol carboxypeptidases. Such enzymes can be produced by yeast fungi, or they may be of animal, vegetable or microbial origin.

A particularly expedient enzyme is carboxypeptidase Y from yeast fungi (CPD-Y). This enzyme is described in the earlier applications i.a. with reference to Johansen et al. (Ref. 8) who developed a particularly expedient purification method by affinity chromatography on an affinity resin comprising a polymeric resin matrix with coupled benzylsuccinyl groups. CPD-Y, which is a serine enzyme, is characterized by having the above relation between the different enzymatic activities at pH 9 and by having no endopeptidase activity. Another advantage of CPD-Y is that it is available in large amounts and displays relatively great stability. Further details are given in Ref. 7 and 11.

In addition to CPD-Y, which is the preferred enzyme at present, the process of the invention is feasible with other carboxypeptidases, such as those listed in the following survey:

| Enzyme | Origin |
|---|---|
| | Fungi |
| Penicillocarboxypeptidase S-1 | Penicillium janthinellum |
| Penicillocarboxypeptidase S-2 | Penicillium janthinellum |
| Carboxypeptidase(s) from | Aspergillus saitoi |
| Carboxypeptidase(s) from | Aspergillus oryzae |
| | Plants |
| Carboxypeptidase(s) C | Orange leaves |
| | Orange peels |
| Carboxypeptidase $C_N$ | Citrus natsudaidai Hayata |
| Phaseolain | French bean leaves |
| Carboxypeptidase(s) from | Germinating barley |
| | Germinating cotton plants |
| | Tomatoes |
| | Watermelons |
| | Bromelain(pineapple)powder |

The close relationship between a number of the above carboxypeptidases is discussed by Kubota et al. (Ref. 12).

The process of the invention can in principle be carried out with any natural, semi-synthetic or synthetic insulin as substrate component.

It should be mentioned that ionizable groups which are present in the individual amino acids, which are constituents of the insulin starting material, if desired, may be blocked in a manner known per se, depending upon the type of the group. However, this is absolutely not necessary, which is precisely one of the advantages of the present process. If for some reason it should be desired to protect the functional groups, suitable protective groups may be found in the above-mentioned applications, in particular WO 80/02151.

The second participant in the reaction is the so-called amine component which is selected from the group consisting of (a) amino acids of the formula

H—B—OH wherein B is an amino acid residue, (b) optionally N-substituted amino acid amides of the formula

H—B—NR$^1$R$^2$ wherein B is an amino acid residue and R$^1$ and R$^2$ are independently selected from the group consisting of hydrogen, amino, hydroxy, alkyl, cycloalkyl, aryl, heteroaryl, and aralkyl or R$^1$ and R$^2$ together with the nitrogen atom form a heterocyclic group which may contain a further hetero atom, and (c) amino acid esters, thioesters or selenoesters of the formula H—B—OR$^3$, H—B—SR$^3$ or H—B—SeR$^3$ wherein B is an amino acid residue and R$^3$ represents alkyl, cycloalkyl, aryl, heteroaryl or aralkyl.

The amino acid forming part of the amine component may be any of the known amino acids, e.g. leu, ile, ala, gly, ser, val, thr, lys, arg, asn, glu, gln, met, phe, tyr, trp or his.

In this context "alkyl" means straight chain or branched alkyl, preferably with 1 to 6 carbon atoms, e.g. methyl, ethyl, propyl, isopropyl, butyl, isobutyl, tert.butyl, amyl, hexyl and the like.

"Cycloalkyl" preferably means $C_3$–$C_8$ cycloalkyl, e.g. cyclopropyl, cyclobutyl, etc.

"Aryl" is preferably phenyl and the like.

"Aralkyl" means benzyl, phenethyl, and the like. As stated the groups R$^1$ and R$^2$ may be the same or different.

"Heteroaryl" as well as the heterocyclic group which may be formed by R$^1$, R$^2$ and the nitrogen atom are represented by e.g. pyridyl, pyrrolidyl, pyrimidinyl, morpholinyl, pyrazinyl, imidazolyl, etc.

All of these groups may be substituted with substituents which are inert with relation to the enzyme, e.g. halo (fluoro, chloro, bromo, iodo), nitro, alkoxy (methoxy, ethoxy, etc.), or alkyl (methyl, ethyl, etc.).

Thus in case of all types of esters the group OR$^3$ is preferably selected from alkoxy groups, such as methoxy, ethoxy or t-butoxy, phenyloxy, and benzyloxy groups. The groups may optionally be substituted with inert substituents, such as nitro groups (p-nitrobenzyloxy).

It is seen that in case of amides, when R$^1$=hydrogen, R$^2$=hydrogen represents the free amide, while R$^2$=OH is a hydroxamic acid, R$^2$=amino is a hydrazide, and R$^2$=phenyl represents an anilide.

As stated above, the process of the invention is carried out at pH 7.0 to 10.5, preferably at pH 7.5 to 10.5. The preferred pH-value, which is often within a very narrow range, depends upon the pH-optima and pH-minima, respectively, for the different enzymatic activities of the enzyme used, it being understood that the

Amino Acid Analyses

Samples for amino acid analysis were hydrolyzed in 6M HCl at 110° C. in vacuum for 24 hours, and analyzed on a Durrum D-500 amino acid analyzer. The amino acid compositions were based on the known content of aspartic acid and glycine. Thr, Lys and Ala are the only amino acids affected by the reactions. The values of these amino acids for porcine (human) insulin are: Thr=1.93 (2.87), Lys=0.97 (0,98) and Ala=2.00 (1.05). The amount of unconverted porcine insulin in the reaction mixture was determined from the alanine analysis of the insulin pool after chromatography on "Sephadex G-50". The coupling yield is defined as the amount of a given product divided with the amount of all insulin consumed in the reaction.

Carboxypeptidase A Digestions (examples 2 and 3 below)

To 100 μl of a solution of insulin or insulin derivatives (0.7 mg/ml) in 0.1M Tris-HCl, pH 7.5, was added 10 μg of carboxypeptidase A. After digestion at room temperature for 6 hours the reaction was stopped by addition of an equal volume of 0.5M HCl, and the release of amino acids determined by amino acid analysis.

Enzymatic digestion of insulin derivatives (example 4)

Digestion of various insulin derivatives with carboxypeptidases A and Y were performed in a 0.5M Tris buffer, pH 7.5 at room temperature using approximately 1.5 mM insulin and 5 μM carboxypeptidase. Reaction times were 3 hours with CPD-A and 1.5 hours with CPD-Y. Under these conditions maximal release of C-terminal amino acids were obtained. After acidification with HCl, the aliquots were applied directly on the amino acid analyzer.

The sequence of the C-terminal portion of the various insulin derivatives were determined after trypsin digestion and reaction of the digest with Dansyl chloride, followed by identification of the Dansyl peptides. Digestion of insulin derivatives with trypsin was performed in 0.1M NaHCO$_3$ at pH 8.2, using 1 mM insulin, 40 μM DPCC-trypsin and an incubation time of 1 hour. Preliminary experiments on porcine insulin had indicated that these conditions were sufficient for complete release of the C-terminal alanyl residue from the B-chain. The released amino acids or dipeptides were dansylated as follows: A 100 μl sample of the tryptic digestion mixture was quenched by addition of 100 μl 0.5M HCl. The aliquots were evaporated to dryness and redissolved in 100 μl 0.1M NaHCO$_3$, pH 8.2, 100 μl Dansyl chloride (5 mg/ml) in acetone was added, and the reaction mixture incubated for 2 hours at 37° C. The reaction mixture was then analyzed by HPLC, using the Waters liquid chromatography system, consisting of a Model U6K injector, two Model 6000 A pumps, a Model 660 Solvent Programmer, a Model 450 UV detector, a Waters Data Module and a Waters Radial Compression Module (RCM 100) housing equipped with a Waters Radial Pak A (C-18 reverse phase) column.

The following standard compounds were synthesized: Dns—Ala—OH, Dns—Thr—OH, Dns—Ala—Thr—OH, Dns—Thr—Thr—OH, Dns—Thr—NH$_2$, Dns—Thr—Thr—NH$_2$ and Dns—Ala—NH$_2$. Using the procedure described above for the dansylation of insulin digestions, three of these derivatives could by synthesized from H—Ala—OH, H—Thr—OH and H—Thr—NH$_2$. The dansylated dipeptides were synthesized via Dns—Ala—OMe and Dns—Thr—OMe: 1 mmol H—Ala—OMe•HCl was dissolved in 0.1M NaHCO$_3$, 5 mmol of Dansyl chloride was added, and the reaction mixture incubated for 2 hours. The Dns—Ala—OMe was extracted from the reaction mixture with ethyl acetate and evaporated to dryness. It was demonstrated by HPLC that the isolated material was pure. The same procedure was used to synthesize Dns—Thr—OMe. Using procedures for enzymatic peptide synthesis similar to those previously described (Ref. 7 and 11) these two compounds were then coupled to H—Thr—OH, giving Dns—Ala—Thr—OH and Dns—Thr—Thr—OH and H—Thr—NH$_2$, giving Dns—Ala—Thr—NH$_2$ and Dns—Thr—Thr—NH$_2$. The conditions were as follows: 5 mM substrate, 0.5M nucleophile, 0.1M KCl, 2 mM EDTA, 1 μm CPD-Y, pH 9.0, 10% ethanol. All seven Dansyl derivatives could readily be separated by HPLC using two different programs.

EXAMPLE 1

(Background investigations)

Porcine insulin was incubated with carboxypeptidase-Y at 25° C. and pH 5-7, a pH-range where the enzyme exhibits maximal peptidase activity. Thereby the following amino acids from the C-terminal of the B-chain were released: 1.0 Alanine, 1.0 Lysine, 1.0 Proline, 1.0 Threonine, 1.0 Tyrosine, and 2.0 Phenylalanine. At position B-23 (glycine) carboxypeptidase-Y stops, and hence complete release of the first seven amino acids in the B-chain of insulin can be achieved. Surprisingly, the C-terminal asparagine (A-21) of the A-chain is not released at all. At pH 9.5 the C-terminal alanine of the B-chain is released much faster than the following amino acids. Importantly, the Leu—Tyr (B15-16) bond was not hydrolyzed since the purified CPD-Y preparations used were free of protease A (endopeptidase) in contrast to many preparations commercially available from other sources, cf. Ref. 11.

EXAMPLE 2

(conversion of porcine insulin into human insulin using threonine amide as amine component without isolation of insulin amide intermediates)

To a solution of zinc-free porcine insulin (2 mM) in 10 mM EDTA, 0.1M KCL containing 0.5M L-Threonine amide at pH 9.5 and 25° C. was added carboxypeptidase-Y (50 μM). The pH of the reaction was kept constant by addition of 0.5M NaOH using a pH-stat. To follow the reaction aliquots at various time were taken and the reaction stopped by addition of 6M HCl to bring the pH to 1-2. The sample was then chromatographed on "Sephadex ®G-50" (1×30 cm) equilibrated with 1M acetic acid in order to separate insulin from the enzyme and free amino acids. The insulin containing fractions were then lyophilized, and the amino acid composition determined as described above.

Figure 1:
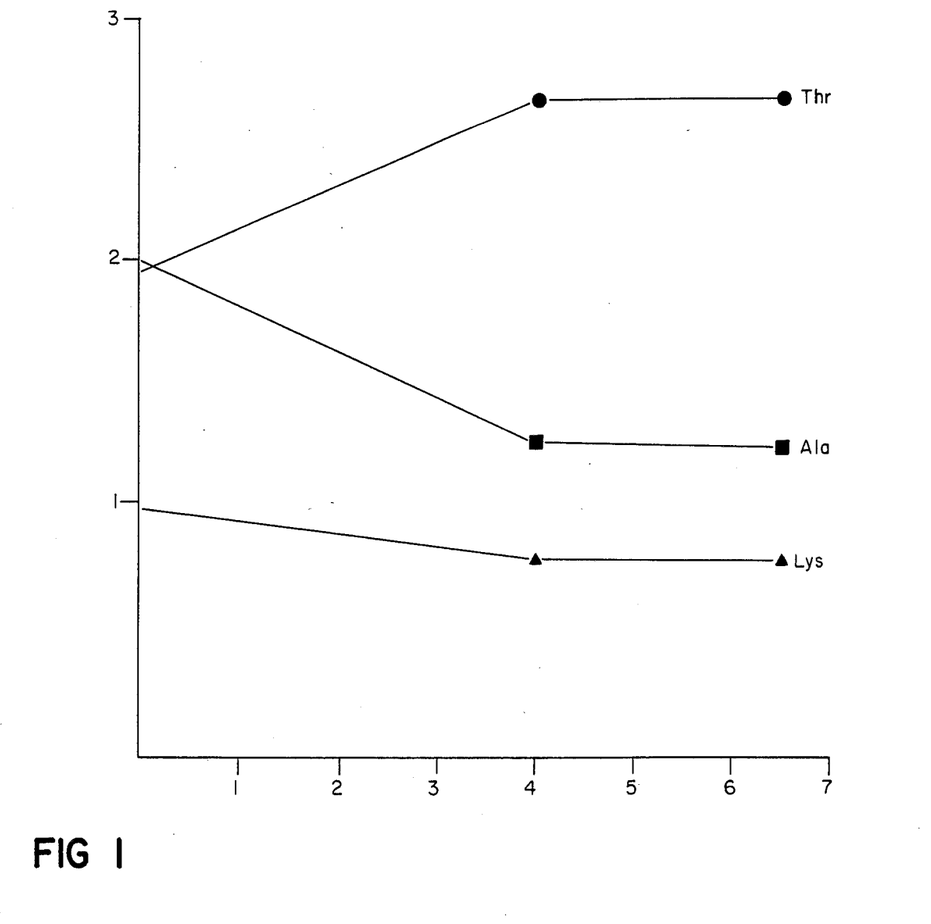
FIG. 1 shows the reaction course when porcine insulin is reacted with L-Threonine amide using CPD-Y as catalyst. The amino acid analysis is plotted vs. the reaction time.

The reaction course is shown in FIG. 1. From the amino acid analysis it was calculated that the threonine content increased by 0.7 moles per mole of insulin, whereas 0.8 moles of alanine was lost together with 0.2 moles of lysine (FIG. 1). These results suggested that after 6.5 hours of reaction 20% of the porcine insulin was unreacted, while 20% of the insulin had in addition to the alanine also lost the next amino acid lysine. The loss of 0.8 moles of alanine was accompanied by incorporation of 0.7 moles of threonine.

The reaction products were further analyzed by carboxypeptidase A digestions. Carboxypeptidase A liberates only amino acids with free α-carboxyl groups and does not liberate lysine. In accordance with this specificity carboxypeptidase A digestion of porcine insulin only releases alanine and asparagine from the C-terminal ends of the B-chain and A-chain, respectively. Hence incubation of the insulin sample obtained after 6.5 hours of reaction (FIG. 1) should in addition to asparagine only release alanine in an amount corresponding to the fraction of unreacted porcine insulin. Surprisingly, besides alanine also threonine was released in amounts equivalent to the threonine amide incorporated to form the intermediate human insulin amide. This must be due to the fact that in addition to its peptidase and esterase activity carboxypeptidase-Y also has peptide amide hydrolase activity, cf. Ref. 11. Apparently, during the reaction of porcine insulin in the presence of carboxypeptidase-Y the C-terminal alanine is initially exchanged with threonine amide in a transpeptidation reaction to form human insulin amide, which then is hydrolyzed by carboxypeptidase-Y to give human insulin in a total yield of about 60%, 20% unreacted porcine insulin and 20% are other break down products. Other experiments have confirmed this sequence of reactions. Using less enzyme or shorter reaction time, carboxypeptidase A digestion of the reaction products showed less threonine release compared to threonine incorporation i.e. predominant human insulin amide was formed.

To separate the reaction products, the sample obtained after 6.5 hours of reaction (FIG. 1) was subjected to high performance liquid chromatography using a "Lichrosorb RP-18", 5 μm, reverse phase column (0.4×30 cm) and a Waters Model 6000A pump and Model 450 UV detector operating at 220 nm. The eluent was 28.75% CH$_3$CN in 5 mM tartrate buffer pH 3.0 containing 5 mM nBu—SO$_3$Na and 50 mM Na$_2$SO$_4$ (cf. Inouye, Ref. 4). The flow rate was 1.0 ml/min. Using this system human and porcine insulin could not be separated but all other by-products were removed. The amino acid analysis of the chromatographed material is shown in Table I. The analysis is in excellent agreement with the composition expected from the theoretical values. The content of 2.6 moles of threonine and 1.3 moles of alanine suggests that the sample contained about 70% human and 30% porcine insulin.

TABLE I

| Amino Acid | Amino Acid Composition of Insulin | | |
|---|---|---|---|
| | Moles Amino Acid Mole Insulin | Sequence Porcine | Human |
| Aspartic acid | 3.1 | 3 | 3 |
| Threonine | 2.6 | 2 | 3 |
| Serine | 3.1 | 3 | 3 |

TABLE I-continued

| Amino Acid | Amino Acid Composition of Insulin | | |
|---|---|---|---|
| | Moles Amino Acid Mole Insulin | Sequence Porcine | Human |
| Glutamic acid | 7.2 | 7 | 7 |
| Proline | 1.2 | 1 | 1 |
| Glycine | 4.0 | 4 | 4 |
| Alanine | 1.3 | 2 | 1 |
| Valine | 3.5* | 4 | 4 |
| Isoleucine | 1.4* | 2 | 2 |
| Leucine | 6.1 | 6 | 6 |
| Tyrosine | 3.6 | 4 | 4 |
| Phenylalanine | 3.0 | 3 | 3 |
| Histidine | 1.9 | 2 | 2 |
| Lysine | 1.0 | 1 | 1 |
| Arginine | 1.0 | 1 | 1 |

*Low values due to incomplete hydrolysis

EXAMPLE 3

(Conversion of porcine insulin into human insulin using threonine methylester as amine component without isolation of intermediates)

To a solution of zinc-free porcine insulin (8 mM) in 10 mM EDTA, 0.1M KCl containing 0.5M-L-Threonine methylester at pH 9.5 and 25° C. was added carboxypeptidase-Y (60 μM). The pH of the reaction was kept constant by addition of 0.5M NaOH using a pH-stat. To follow the reaction aliquots at various time were taken and the reaction stopped by addition of 6M HCl to bring the pH to 1–2. The sample was then chromatographed on "Sephadex G-50" (1×30 cm) equilibrated in 1M acetic acid in order to separate insulin from the enzyme and free amino acids. The insulin containing fractions were then lyophilized, and the amino acid composition determined as described above.

Figure 2:
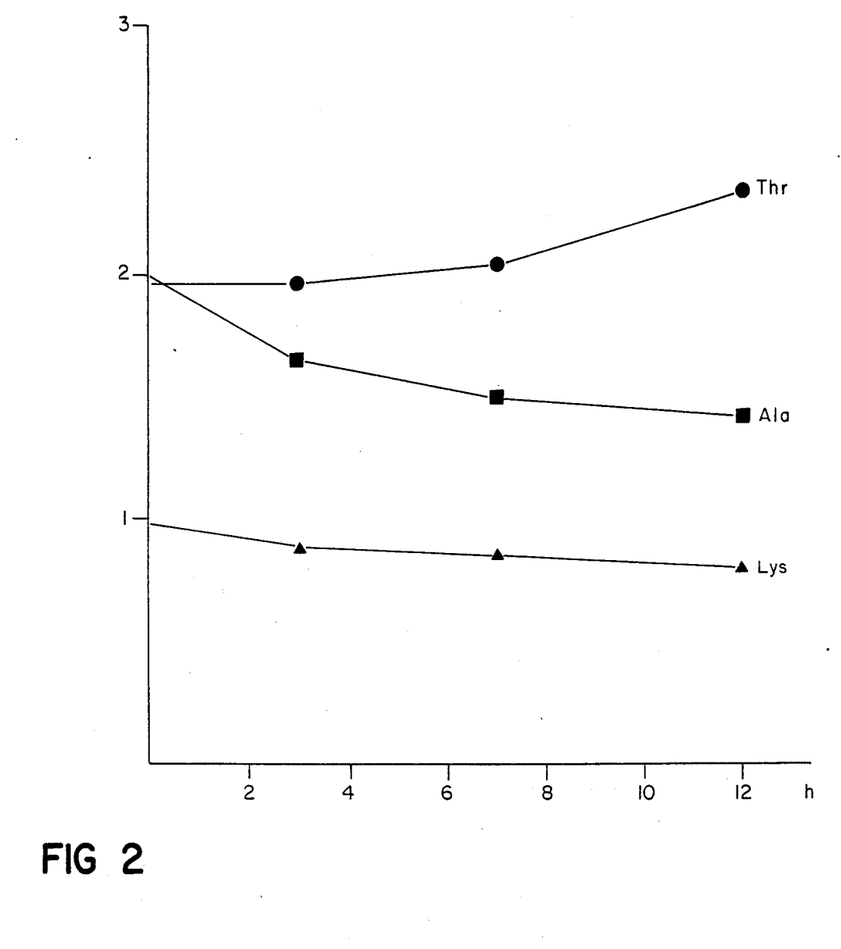
FIG. 2 shows the similar reaction course when L-Threonine methyl ester is used as amine component.

The reaction course is shown in FIG. 2. The results of this reaction are very similar to those described above using threonine amide: Threonine is incorporated concomitantly with the release of alanine and a small amount of lysine. Carboxypeptidase A digestion of the sample after 17 hours of reaction liberated both alanine and threonine, suggesting that the C-terminal alanine of the B-chain is first exchanged with threonine methylester to form human insulin monomethylester, which is subsequently hydrolyzed by carboxypeptidase-Y to give human insulin. While the reaction qualitatively is similar to that described above for threonine amide, the final reaction mixture contains only 40% human insulin, 40% of the porcine insulin was not converted and 20% was hydrolyzed to other products.

EXAMPLE 4

(Conversion of porcine insulin into human insulin using threonine amide as amine component and with isolation of intermediate insulin amides).

To a solution of zinc free porcine insulin (2 mM) in 2 mM EDTA, 0.1M KCl and 1.5M guanidine hydrochloride and containing 0.5M threonine amide (L—Thr—NH$_2$) at pH 7.5 anf 25° C. was added CPD-Y (15 μM). The pH of the reaction was kept constant by addition of 0.5M NaOH using a pH-stat. To follow the reaction course aliquots at various times were taken and the reaction was quenched after 2 hours by adjusting the pH to 1.5–2.0 with 1M HCl. The insulin fraction was separated from the enzyme and low molecular weight compounds by chromatography on "Sephadex ®G-50 fine" (1×30 cm) equilibrated with 1M acetic acid and was lyophilized. Amino acid analysis on the lyophilized "insulin pool" is described above indicated that 78% of the porcine insulin had been consumed in the reaction.

In order to further analyse the reactants present in the "insulin pool" ion exchange chromatography on "DEAE-Sephadex ®A-25" was performed essentially as described by Morihara et al (Ref. 5). The lyophilized insulin sample (75 mg) was dissolved in 0.01M Tris, 2.5M urea, 0.05M NaCl, pH 7.5 and applied to a "DEAE Sephadex ®A-25" column (0.5×25 cm) equilibrated with the same buffer. The insulin was eluted with a NaCl gradient from 0.05 to 0.30M in the same buffer and 8 ml fractions were collected on a "Sephadex ®G-25" column and lyophilized.

Figure 3:
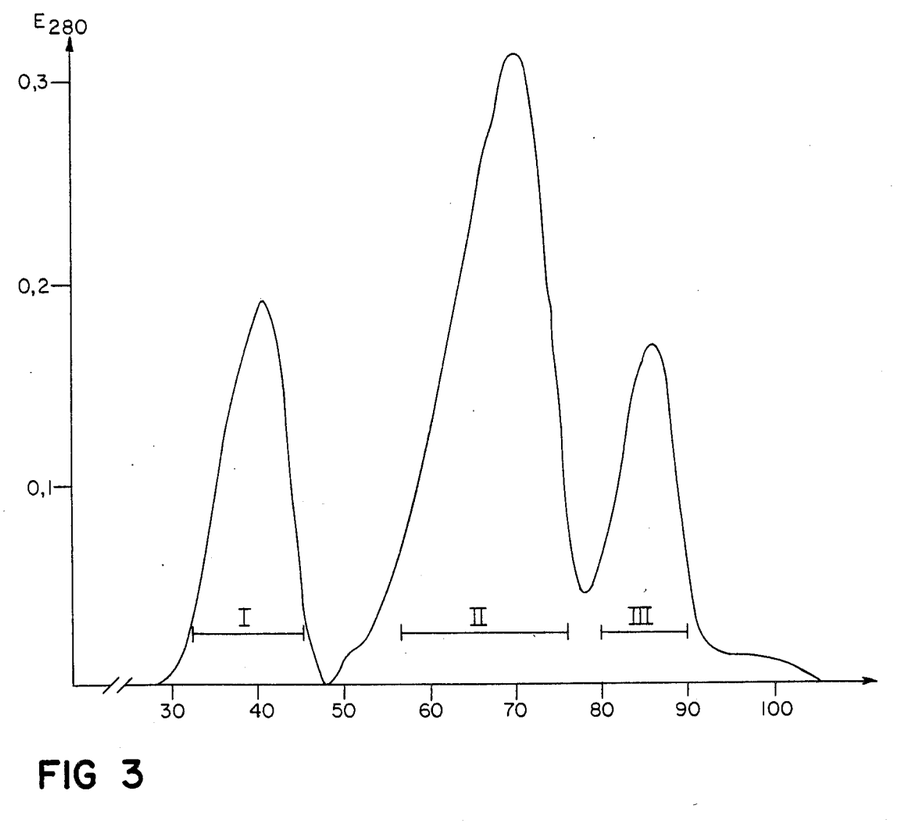
FIG. 3 shows an elution profile from an ion exchange chromatography on the product of reaction between porcine insulin and threonine amide.

The elution profile is shown in FIG. 3, where three peaks are observed. Also stated is the amino acid compositions of the individual peaks and the peak compositions as a result of digestion experiments performed with CPD-Y and CPD-A as described above. Since only the C-terminal of the B-chain of insulin is involved in these reactions, —Pro—Lys—Ala—OH is used as an abbreviation of porcine insulin. Other insulin derivatives are thus abbreviated accordingly: —Pro—Lys—Thr—OH=human insulin, —Pro—Lys—Thr—NH$_2$ =human insulin amide, etc. It is seen that at pH 7.5 which was used for the reaction, and where the amidase activity of CPD-Y generally is lower than the peptidase activity, the peptide amide formed is sufficiently stable since peak I comprised about 20% of the total insulin pool. In the reaction about 75% of the porcine insulin starting material has been converted. However, since the threonine content of peak I (3,65) is larger than the 3.0 in human insulin, it is evident that the initial transpeptidation product (—Pro—Lys—Thr—NH$_2$) is not sufficiently stable to avoid an oligomerisation under formation of (—Pro—Lys—Thr—Thr—NH$_2$).

This formation of a mixture of amide intermediates might on the face of it indicate that a homogenous human insulin would not be formed by the earlier described deamidation step by means of CPD-Y, since deamidation would be expected to result in a mixture of —Pro—Lys—Thr—OH and —Pro—Lys—Thr—Thr—OH. However, when the peak I mixture was subjected to a deamidation treatment with 10 μM CPD-Y at pH 10.0 in 0.1M HCl, 2 mM EDTA for 20 minutes, surprisingly almost pure human insulin was obtained. The experiment proceeded as follows:

After separation of the reacted insulin from enzyme and low molecular weight material by chromatography on "Sephadex G-50", the material was chromatographed on "DEAE Sephadex A-25" using procedures identical to those in FIG. 3. The reaction product eluted in Peak II as expected, while the unreacted material (<10%) eluted in Peak I. No Peak III was present, i.e. no insulin derivatives without lysine were formed. As indicated from the results in Table II below obtained by CPD-A, CPD-Y and trypsin digestion, only the threonine content was significantly affected by these reactions. This is in agreement with the expected absence of peptidase activity of CPD-Y at this pH.

The amino acid composition of Peak II from the deamidation reaction is close to the analysis of human insulin: Thr=2.87, Ala=1.05, Lys=0.98. The digestion of the deamidated product with CPD-Y, CPD-A and trypsin indicated that the sample contain 90–95% of pure human insulin. This suggests that the insulin derivative —Pro—Lys—Thr—Thr—NH$_2$ reacts almost exclusively via the peptidyl-amino-acid-amide hydrolase activity while —Pro—Lys—Thr—NH$_2$ reacts mostly via the amidase activity. The overall yield for the conversion of porcine insulin to human insulin is approximately 30% based on the amount of converted insulin.

TABLE II

Amino acid composition of Peaks I, II, and III from FIG. 3 and Peak II obtained after deamidation treatment of Peak I fraction

| | Peak I | Peak II | Peak III | Peak II obtained after deamidation of Peak I |
|---|---|---|---|---|
| Aspartic acid | 2.99 | 2.99 | 3.01 | 3.01 |
| Threonine | 3.62 | 2.52 | 2.50 | 2.79 |
| Serine | 2.93 | 2.92 | 2.92 | 2.93 |
| Glutamine acid | 6.88 | 7.16 | 7.18 | 7.01 |
| Proline | 1.00 | 0.98 | 0.71 | 0.87 |
| Glycine | 4.00 | 4.00 | 4.00 | 4.00 |
| Alanine | 1.16 | 1.52 | 1.03 | 1.09 |
| Valine | 2.42 | 2.82 | 2.81 | 2.50 |
| Ileucine | 0.94 | 1.04 | 1.09 | 1.19 |
| Leucine | 5.80 | 6.21 | 6.18 | 6.10 |
| Tyrosine | 3.80 | 3.86 | 3.67 | 4.02 |
| Phenylalanine | 2.74 | 2.82 | 2.65 | 2.64 |
| Histidine | 1.96 | 1.90 | 1.93 | 1.89 |
| Lysine | 0.99 | 0.74 | 0.06 | 1.01 |
| Arginine | 0.96 | 1.00 | 0.98 | 0.89 |

EXAMPLE 5

(Deamidation of human insulin amide obtained by trypsin-catalyzed condensation of Des-alanine (B30) porcine insulin (DAI) with threonine amide).

In order to substantiate that the advantageous CPD-Y catalyzed deamidation of insulin amides is not limited to insulin amides obtained by the transpeptidation process of the invention, human insulin amide was prepared in accordance with the general teachings of Morihara et al. (EP 17 938 and Ref. 5 and 6). It is noted, however, that while amides are mentioned in EP 17 938 as one among other protecting groups for the carboxyl group in threonine, its applicability has not been proved by examples, the only example dealing with threonine tert. butyl ester.

The reaction is illustrated by the following scheme:

$$DAI \xrightarrow[pH\ 6.5]{Trypsin-THrNH_2} DAI-ThrNH_2 \xrightarrow{CPD-Y} DAIThr$$
$$\longrightarrow DAI$$

This method provides the significant advantage over the method exemplified in EP 17 938, that the enzymatic deamidation is much milder than the acid-catalyzed deesterification according to Morihara et al.

Preparation of DAI—ThrNH$_2$

Threonine amide hydrochloride (400 mg) was suspended in 60% dimethylformamide (DMF) (2 ml). pH was adjusted to 6.5 with pyridine (20 μl) and 6M NaOH (50 μl), Trypsin (100 mg) and DAI (100 mg). After ½ hour the reaction was quenched by addition of formic acid (1 ml). The reaction mixture was fractionated on "Sephadex G-50" with 1M acetic acid. The following fractions were collected:

Trypsin fraction:            60 mg

| | | |
|---|---|---|
| Insulin fraction: | 102 mg | |
| Remainder: | 371 mg | |

The insulin fraction (102 mg) was purified by ion exchange chromatography on "DEAE-Sephadex A-25" equilibrated with 7M urea and eluted with a NaCl gradient according to EP 17938.

Pure human insulin amide (DAI—Thr—NH$_2$) in an amount of 59.2 mg (detected by amino acid analysis) was obtained.

Preparation of DAI—Thr (human insulin)

DAI—Thr—NH$_2$ (11 mg) was dissolved in 1 mM EDTA and 2 mM KCl (2 ml). pH was adjusted to 9.0 by means of 0.5M NaOH (51 μl) and CPD-Y (50 μl, 13.6 mg/ml) was added. After 15 min. the reaction was quenched with 6M HCl (25 μl) and the pH dropped to 1.2. The reaction mixture was separated on "Sephadex G-50" and eluted with 1M acetic acid. 8 mg of human insulin was obtained. The amino acid analysis is shown in Table III below:

TABLE III

| | Amino acid analyses | | |
|---|---|---|---|
| | Human insulin (formula) | DAI | Amide | Human insulin |
| Asp | 3 | 2.97 | 3.05 | 3.04 |
| Thr | 3 | 1.91 | 2.94 | 2.90 |
| Ser | 3 | 2.86 | 2.86 | 2.95 |
| Glu | 7 | 7.27 | 7.23 | 7.04 |
| Pro | 1 | 0.94 | 0.95 | 0.85 |
| Gly | 4 | 4.000 | 4.000 | 4.000 |
| Ala | 1 | 1.00 | 1.00 | 1.04 |
| Cys | 6 | 5.31 | 5.19 | 5.02 |
| Val | 4 | 3.37 | 3.11 | 3.24 |
| Ile | 2 | 1.36 | 1.22 | 1.40 |
| Leu | 6 | 6.28 | 6.20 | 6.13 |
| Tyr | 4 | 3.64 | 3.97 | 3.77 |
| Phe | 3 | 2.82 | 2.92 | 2.83 |
| His | 2 | 1.96 | 1.96 | 1.87 |
| Lys | 1 | 0.94 | 1.00 | 0.95 |
| NH$_3$ | 6 | 8.12 | 6.46 | 6.98 |
| Arg | 1 | 0.98 | 0.99 | 0.87 |
| Thr/Ser | 1.00 | 1.003 (× 3/2) | 1.027 | 0.984 |

REFERENCES

1. Ruttenberg, M.A.: Human insulin: Facile synthesis by modification of porcine insulin, Science 177, 623-25(1972)
2. Gattner, H.-G., Schmitt, E. W., Naithani, V. K., in Semisynthetic peptides and proteins, Eds. RE Offord and C-Di Bello, Academic Press, New York 1978, 181.
3. Obermeier, R., Geiger, R. (1976), Hoppe-Seyler's Z. Physiol. Chem., 357, 759-67.
4. Inouye, K., Watanabe, K., Morihara, K., Tochino, Y., Kanaya, T., Emura, J.: Enzyme-assisted semisynthesis of human insulin, Journal of the American Chemical Society, (1979), vol. 101, 751-52.
5. Morihara, V.: Semi-synthesis of human insulin by trypsin-catalyzed replacement of Ala-B30 by Thr in porcine insulin, Nature, Vol. 280, No. 5721, 1979, 412-13.
6. Morihara, K., Oka, T., Tsuzuki, H., Tochino, Y., Kanaya, T.: Achromobacter protease I-catalyzed conversion of porcine insulin into human insulin, Biochemical and Biophysical Research Comm. Vol. 92, No. 2, 1980, 396-402.
7. Widmer, F., Johansen, J. T.: Enzymatic peptide synthesis carboxypeptides Y catalyzed formation of peptide bonds, Carlsberg Res. Commun, Vol. 44, Apr. 23, 1979, 37-46.
8. Johansen, J. T., Breddam, K., Ottesen, M.: Isolation of Carboxypeptidase Y by affinity chromatography, Carlsberg Res. Commun., Vol. 41, No. 1, 1976, 1-13.
9. Lee, H.-M., Riordan, J. F.: Does carboxypeptidase Y have intrinsic endopeptidase activity? Biochemical and Biophysical Research Comm., Vol. 85, No. 3, 1978, 1135-1142.
10. Obermeier, Rainer: Des-octapeptide-(B23-30)-insulin, starting material for human insulin and analogues; studies on synthesis purification and properties, Eds. RE Offord and C-Di Bello, Academic Press, New York, 1978, 201-11.
11. Breddam, K., Widmer, F., Johansen, J. T.: Carboxypeptidase Y catalyzed transpeptidations and enzymatic peptide synthesis, Carlsberg Res. Comm. Vol. 45, Nov. 4, 1980, p. 237-247.
12. Kubota et al. Carboxypeptidase C$_N$, J. Biochem., Vol. 74, No. 4 (1973), p. 757-770.

We claim:

1. A process for enzymatic replacement of the B-30 amino acid in insulins, characterized by reacting as substrate component the selected insulin Ins-X, wherein X represents the B-30 amino acid,
   with an amine component selected from the group consisting of
   (a) optionally N-substituted amino acid amides of the formula

H—B—NR$^1$R$^2$ wherein B is an amino acid residue and R$^1$ and R$^2$ are independently selected from the group consisting of hydrogen, amino, hydroxy, alkyl, cycloalkyl, aryl, heteroaryl and aralkyl or R$^1$ and R$^2$ together with the nitrogen atom form a heterocyclic group which may contain a further heterd atom, and
   (b) amino acid esters of the formula H—B—OR$^3$, H—B—SR$^3$ or H—B.SeR$^3$ wherein B is an amino acid residue and R$^3$ represents alky, cycloalkyl, aryl, heteroaryl or aralkyl,
in the presence of an L-specific serine or thiol carboxypeptidase enzyme in an aqueous solution or dispersion having a pH from about 7 to 10.5, thereby to form an insulin derivative
   Ins—B—NR$^1$R$^2$, Ins—B—B—NR$^1$R$^2$,
   Ins—B—OR$^3$, Ins—B—SR$^3$ or Ins—B—Ser$^3$.

2. The process according to claim 1, characterized by using as the carboxypeptidase enzyme a serine or thiol carboxypeptidase from yeast or of animal, vegetable or microbial origin.

3. The process according to claim 2, characterized by using carboxypeptidase Y from yeast as the carboxypeptidase enzyme.

4. The process according to claim 3, characterized by using a carboxypeptidase Y which has been purified by affinity chromatography on an affinity resin comprising a polymeric resin matrix with a plurality of coupled benzylsuccinyl groups.

5. The process according to claim 2, characterized by using a carboxypeptidase enzyme selected from the group consisting of penicillocarboxypeptidase S-1 and S-2 from Penicillium janthinellum, carboxypeptidases from Aspergillus saitoi or Aspergillus oryzae, carboxypeptidases C from orange leaves or orange peels, carboxypeptidase $C_N$ from Citrus natsudaidai Hayata, phaseolain from french bean leaves, carboxypeptidases from germinating barley, germinating cotton plants, tomatoes, watermelons and Bromelain(pineapple)powder.

6. The process according to claim 1, characterized by using an immobilized carboxypeptidase enzyme.

7. The process according to claim 1, characterized by maintaining the pH in the solution or dispersion at 7.5 to 10.5.

8. The process according to claim 1, characterized by using an organic solvent selected from the group consisting of alkanols, dimethyl sulfoxide, dimethyl formamide, dioxane, tetrahydrofurane, dimethoxy ethane, ethylene glycol and polyethylene glycols.

9. The process according to claim 1, characterized by using an aqueous solution or dispersion containing urea or guanidine hydrochloride in a concentration of up to 3 molar.

10. The process according to any of claims 1, or 2, characterized in that the substrate component is porcine insulin and the amino acid forming part of the amine component is threonine, the amine component being threonine amide.

11. The process of claim 1 further comprising cleaving from said insulin derivative a group $—NR^1R^2$, $—B—NR^1R^2$, $—OR^3$, $—SR^3$, or $SeR^3$.

12. The process according to claim 11 characterized in that the group $—NR^1R^2$, $—B—NR^1R^2$, $—OR^3$, $—SR^3$ or $—SeR^3$ is removed by treating said insulin derivative with an L-specific serine or thiol carboxypeptidase enzyme from yeast or of animal, vegetable or microbial origin in an aqueous solution or dispersion having a pH from about 7 to about 10.5.

* * * * *